US00PP29355P2

(12) United States Plant Patent
Higaki

(10) Patent No.: US PP29,355 P2
(45) Date of Patent: Jun. 5, 2018

(54) ***HYDRANGEA* PLANT NAMED 'BCHY-14.003'**

(50) Latin Name: ***Hydrangea macrophylla* (Thunb.)**
Varietal Denomination: BCHY-14.003

(71) Applicant: Harrison M. Higaki, San Mateo, CA (US)

(72) Inventor: Harrison M. Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days. days.

(21) Appl. No.: 15/530,548

(22) Filed: Jan. 27, 2017

(51) Int. Cl.
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — James R. Cypher; Charles R. Cypher

(57) ABSTRACT

A new and distinct cultivar of *Hydrangea macrophylla* (Thunb.) named 'BCHY-14.003' originated as a controlled cross between varieties. The variety 'BCHY-14.003' has attractive inflorescences with relatively small sepalous florets, bi-color sepals, showy inflorescences, a compact growth habit and good commercial characteristics, including long-lasting infloresences.

4 Drawing Sheets

Botanical classification: *Hydrangea macrophylla* (Thunb.) 'BCHY-14.003'.

Variety denomination: 'BCHY-14.003'.

BACKGROUND OF THE INVENTION

This invention relates to a new and distinct cultivar of the Saxifragaceae family. The botanical name of the plant is *Hydrangea macrophylla* (Thunb.) 'BCHY-14.003'.

The new cultivar originated as a seedling from a controlled cross between the patented variety 'BC9.2'—U.S. Plant Pat. No. 23,758—which was the seed parent and the variety known to the inventor as 'Charm' which was the pollen parent. The seed parent, 'BC9.2', has large attractive inflorescences, florets with a distinct pigmentation pattern, and desirable characteristics for commercial production of ornamental plants for growing and transport in pots.

The variety 'BCHY-14.003' has relatively small sepalous florets and the upper sides of the sepals of the sepalous florets are predominantly white with a pigmented outer rim. On the under sides of the sepals of the sepalous florets the pigmentation bleeds towards the center of the floret as the floret matures. 'BCHY-14.003' has compact, attractive inflorescences with relatively small sepalous florets. 'BCHY-14.003' also has a compact growth habit which makes it suitable for growing in 4" pots. The pigmentation pattern of the upper sides of the sepals is long lasting. Not only does the white pigmentation on the upper sides of the sepals persist with very little of the color of the outer rim bleeding toward the center, but the sepals also resist turning green as the infloresence ages. The inventor observed the pigmentation patern lasting on the upper sides of the sepals for 5 to 6 weeks when the plants were kept at 62 degrees Fahrenheit at night and 70 degrees Fahrenheit during the day. Below is a table comparing the new variety to similar varieties.

TABLE 1

| | New Variety 'BCHY-14.003' | U.S. Plant Patent 23,758 'BC9.2' | U.S. Plant Patent PP20, 705 'Glory' (Pollen Parent of 'BC9.2)' | U.S. Plant Patent PP15,912 'White Robe' |
|---|---|---|---|---|
| Leaf size | 9.0 cm wide × 11.0 cm long | 11 cm wide × 16 cm long | 14.5 cm wide × 18.5 cm long | 16 cm wide × 19 cm long |
| Plant height | 11" in 6" pot. | 17" in 6" pot. | 17" in 6" pot | 17' in 6" pot |
| Stem strength | Strong, but benefits from being staked | Strong, but benefits from being staked | Strong | Strong |
| Sepal Pigmentation | Upper sides of sepals are R.H.S. 155 D (white group) with edges of R.H.S. 59 B (red - purple group). Under side of sepals are R.H.S 155 D (white group) but pigmentation of edges of R.H.S. 59 B (red - purple group) also bleeds toward center of floret as the floret ages. | Both sides of sepals are R.H.S. 155 C (white group) with edges of R.H.S. 63 A (red - purple group). | Upper side of sepals is R.H.S. 155D (white group); Underside of sepals is R.H.S. 155 D (white group) | Both sides of sepals are R.H.S. 155 D(white group). |
| Sepalous Floret Size - Diameter | 40 mm | 50 mm | 45 mm | 65 mm to 75 mm |

The new cultivar 'BCHY-14.003' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BCHY-14.003' remains firmly fixed.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
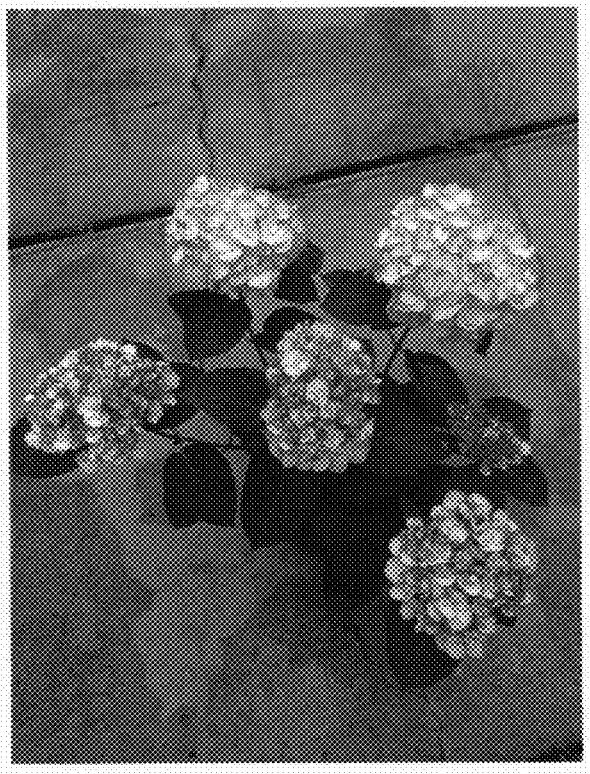
FIG. 1 is a top view of the entire plant showing its form, growth habit, dark green foliage, inflorescence, and the color of its sepals.
Figure 2:
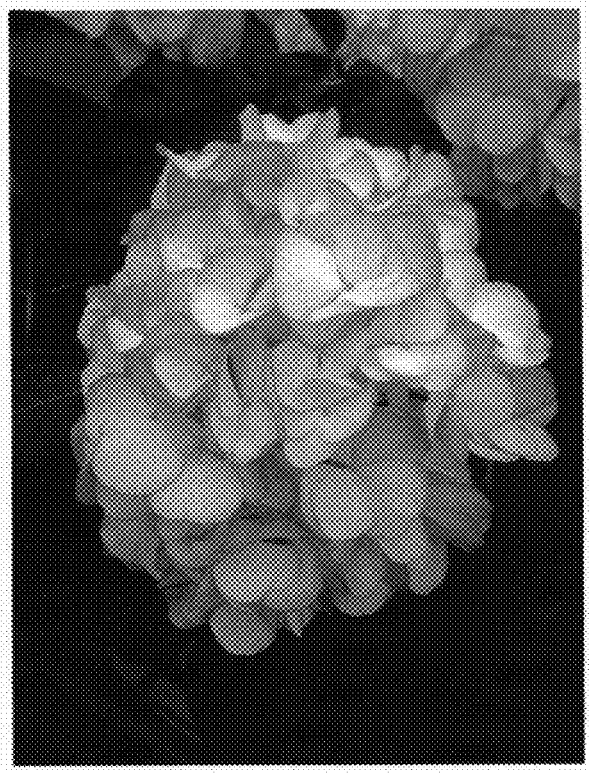
FIG. 2 is a top view of an inflorescence.
Figure 3:
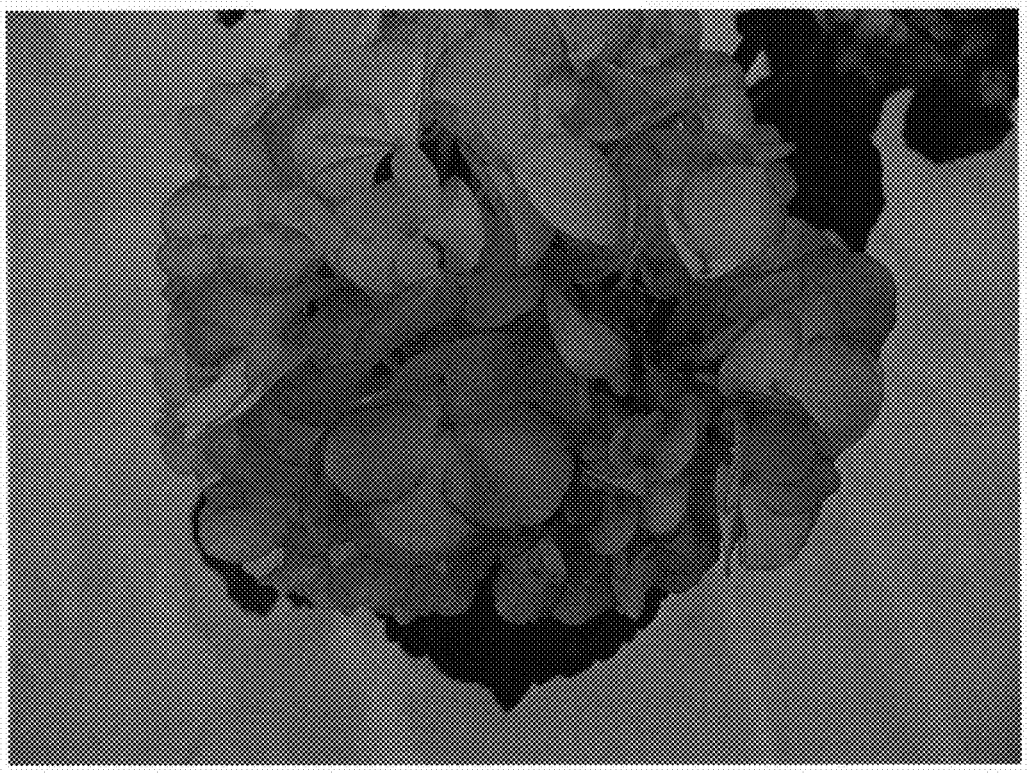
FIG. 3 is a top view of an inflorescence.
Figure 4:
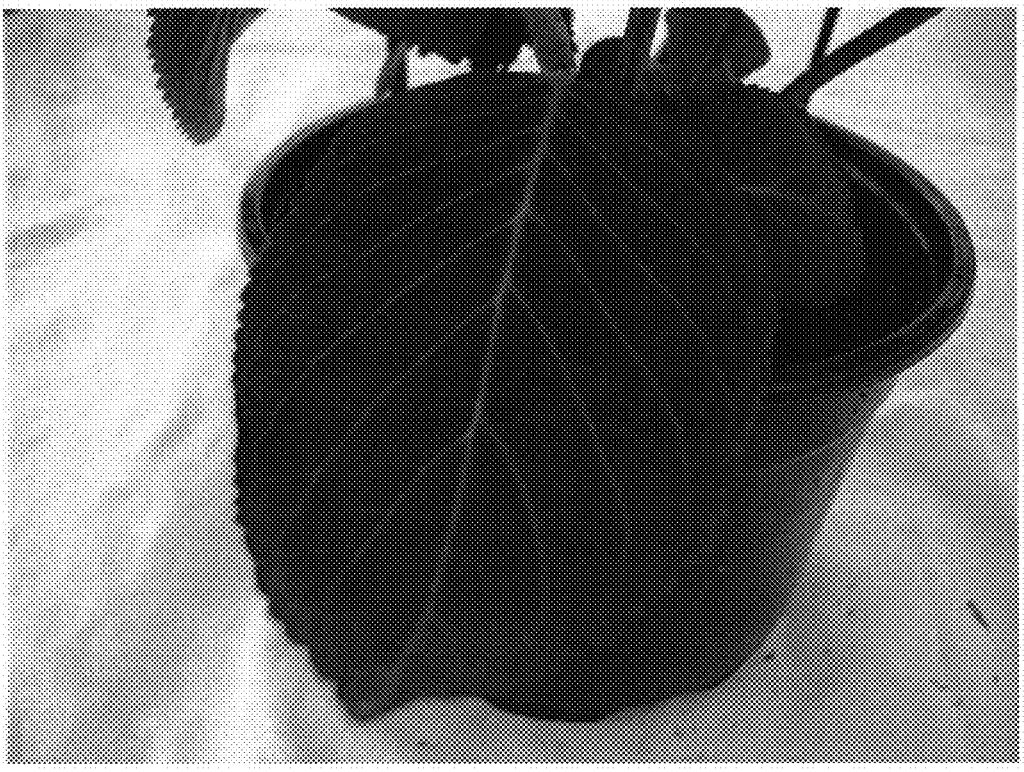
FIG. 4 is a close-up view of the adaxial surface of a mature leaf.
Figure 5:
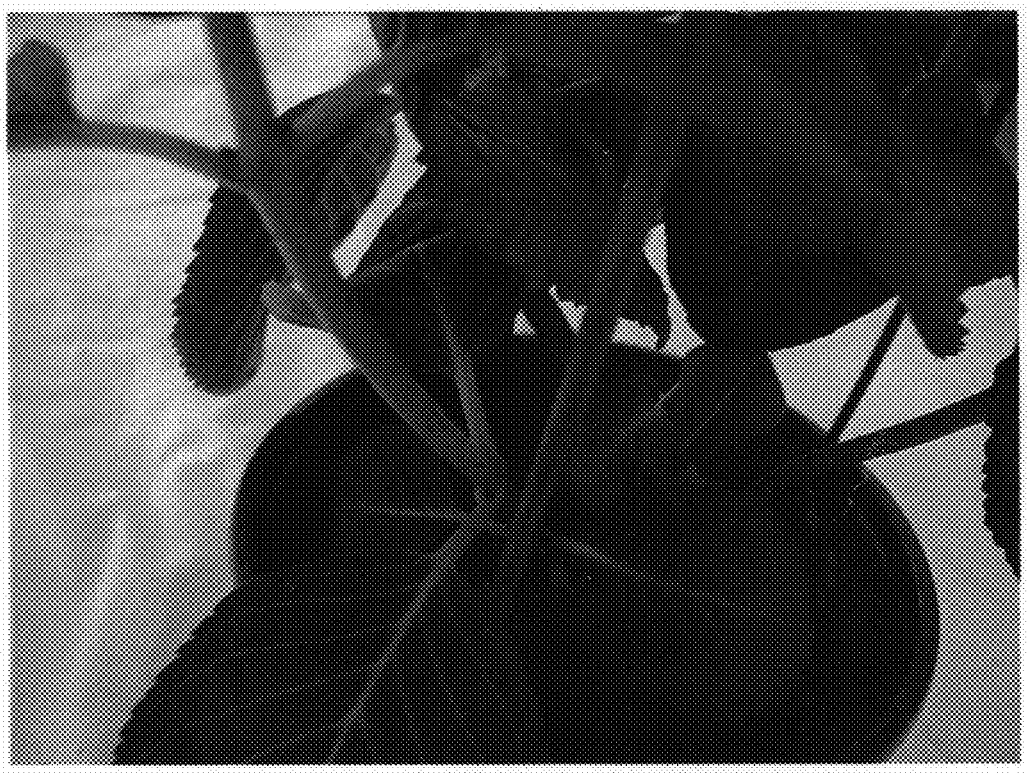
FIG. 5 is a close-up view of the stem of the new variety.
Figure 6:
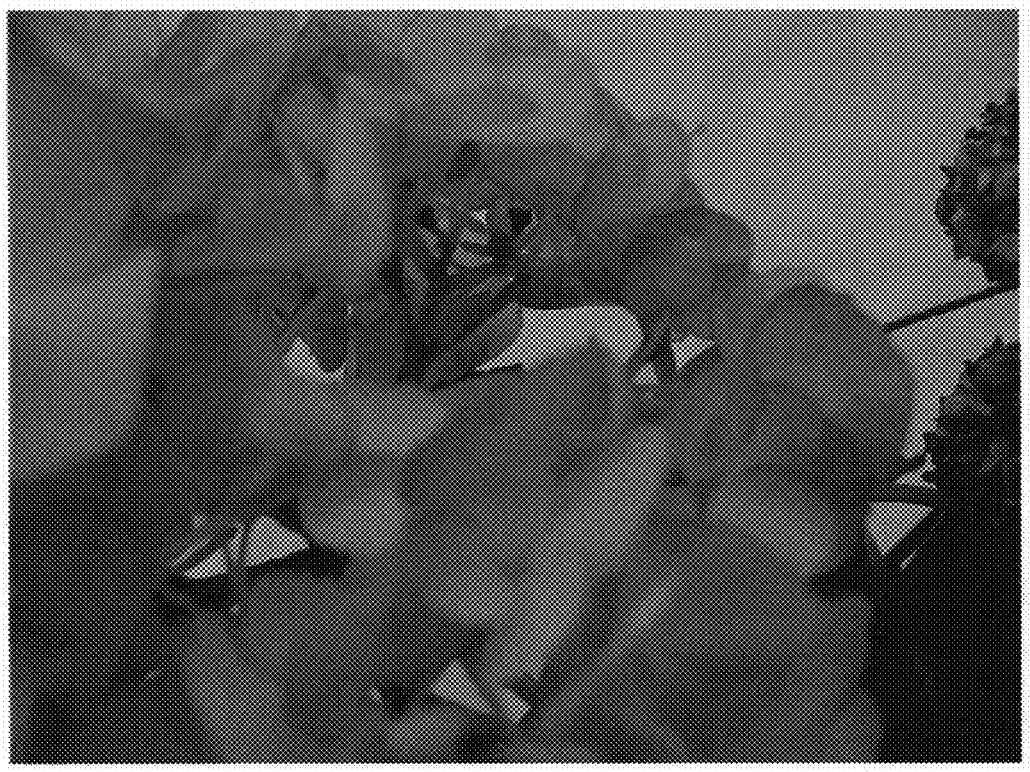
FIG. 6 is a close-up view of the panicle of the new variety.
Figure 7:
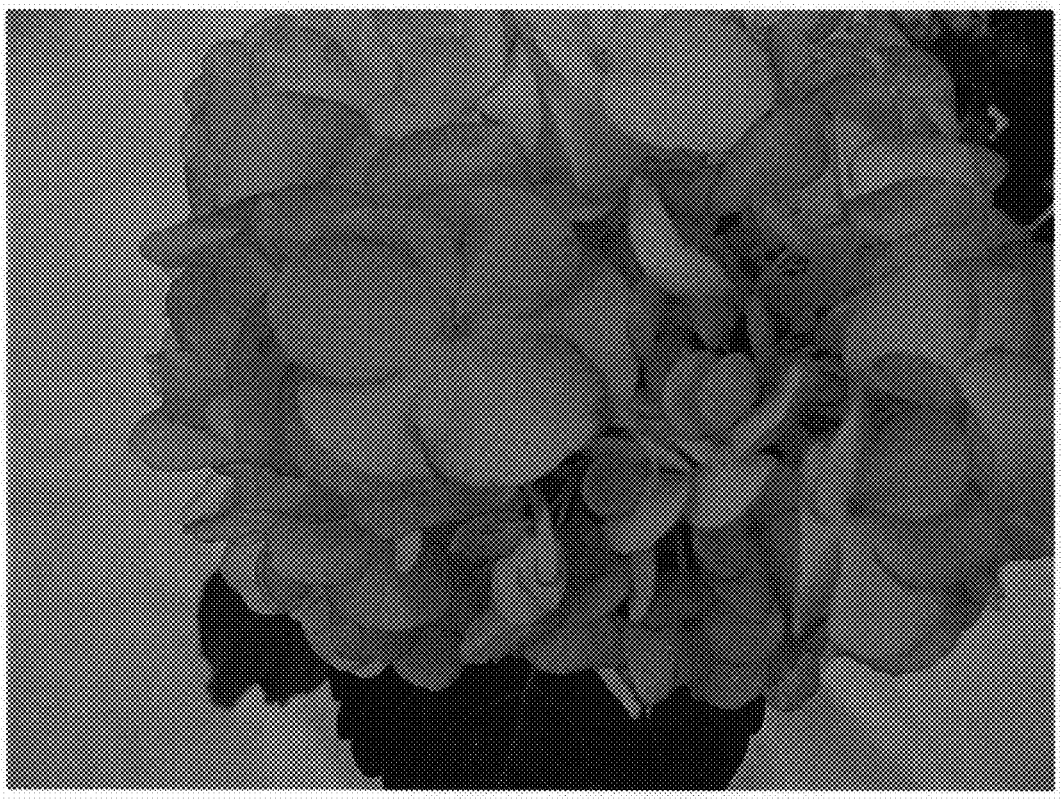
FIG. 7 is a close-up view of a floret.

The plant shown is approximately a year old. The plant started out as cuttings, taken from the stem of a grown plant.

'BCHY-14.003' has not been observed under all possible environmental conditions. The phenotype may vary significantly with variations in environment such as temperature, light intensity, treatment with aluminum and day length. Color determinations were made with The Royal Horticultural Society (R.H.S.) Colour Chart, developed in association with the Flower Council of Holland, located in Lieden.

THE PLANT

Origin: The new cultivar originated as a seedling from a controlled cross between the patented variety 'BC9.2'—U.S. Plant Pat. No. 23,758—which was the seed parent and the variety known to the inventor as 'Charm' which was the pollen parent.

Form: Upright, compact shrub. A typical plant with a mature inflorescence that is ready for sale is approximately 11" high and has a diameter of 13" when grown in a 6" pot with appropriate soil amendments.

Growth: Upright, vigorous growth habit. Inflorescence is showy. The plant branches easily with shoots forming at the base of the plant. Lateral branches are similar in appearance and form to the main stems.

Stems: Lenticels are present. Lenticels are R.H.S. 59 B (red-purple group) and are 1 to 3 mm long. The surface of young stems is glabrous. Stems become woody as they age. The color of typical young stems and young lateral branches is R.H.S. 145 A (yellow-green group). The older portions of the stems are R.H.S. 199 A (grey-brown group). Younger portions of the stems are 6 mm in diameter. Older portions of the stems are 6 mm in diameter.

Foliage: Abundant. Leaves are opposite on stem and lateral branches.

*Shape of leaf.*—Ovate with rounded base and acute apex. Margins are serrate.

*Texture.*—Glabrous; veins dominate on the underside of the leaf and are sunken on the upper leaf surface.

*Color.*—Mature leaves have an upper side that is R.H.S. 147 A (yellow-green group), and an under side that is R.H.S. 138 A (green group). Leaves are pinnately veined. The midvein and veins branching off the midvein are large and prominent on the underside of the leaves. Veins are R.H.S. 145 A (yellow-green group). Leaves are as wide as 9.0 cm and 11.0 cm long. Petioles are smooth and approximately 2.5 cm long and 4 mm wide. Petioles are R.H.S. 145 A (yellow-green group).

BUDS

Form: Globose with 5 to 6 connate, elliptic, smooth petals. The vast majority of buds will develop into sepalous florets. They are approximately 2 mm by 2 mm at full size and do not open.

Aspect: Smooth.

Arrangement: Borne on branched panicles.

INFLORESCENCE

Form: Paniculate. Terminal. As many as 100 individual florets (both sepalous and non-sepalous) per inflorescence. Both sepalous florets and non-sepalous florets borne on the same panicle. Flowers do not produce a fragrance. The peduncle for the inflorescence is strong and upright. A few non-sepalous florets developing early on cymes that are later hidden by the sepalous florets. Florets do not open. Inflorescences are long-lasting, up to six weeks.

Size of inflorescence: Compact and globose Individual inflorescence size is dependent on the number of florets. A typical inflorescence can grow as large as 6" in diameter, and 3" high.

Shape: Clusters of numerous small florets; sepalous florets overlap one another. Sepals are persistent.

Appearance: Showy.

FLORETS

General: Florets do not typically open. Corolla: Generally, for both sepalous and non-sepalous florets there are 5 to 6 petals. Petals are typically 1 mm long and 1 mm wide. Petals range in color from R.H.S. 145 A (yellow-green group) to R.H.S. 155 B (white group) with the non-sepalous florets being the darker green. Lenticels are present on pedicels of both sepalous and non-sepalous florets, lenticels range from 1 mm to 3 mm long and are very narrow. Lenticels merge at pedicel branches. Lenticels are R.H.S. 59 B (red-purple group). Pedicel length for non-sepalous florets is typically 4 mm. Pedicel length of sepalous florets is approximately 12 mm in length for plants of this age. Pedicels of both sepalous and non-sepalous florets continue to elongate as the inflorescence ages. Pedicels are R.H.S. 155 D (white group).

*Stamens.*—Present but undeveloped in unopened florets.

*Stigma.*—Too small to observe as florets do not open.

*Ovary.*—Ovary is partially inferior.

Sepalous florets:

*General.*—Veins dominate on the underside of the sepals.

*Number of sepals.*—5 to 6 sepals per floret, usually 5.

*Aspect of sepals*.—Smooth and glaucescent.

*Shape of sepals*.—Reniform with acuminate apex. Edges are entire, but with much crenation.

*Size of sepals*.—As the florets mature, the sepals enlarge and overlap each other more and more, until, often, there is no space between the sepals. Sepals at maturity are typically 20 mm long and 25 mm wide. Sepalous florets are typically 40 mm in diameter. The upper sides of the sepals are R.H.S. 155 D (white group) with edges of R.H.S. 59 B (red-purple group). Under side of sepals are R.H.S 155 D (white group) but pigmentation of edges of R.H.S. 59 B (red-purple group) on the under sides of the sepals also bleeds toward center of floret as the floret ages. The upper sides of the sepals resist bleeding of the pigmented outer rims toward the center. The sepals of the florets are also resistant to greening as the florets age.

Fruit: None.

Disease and pest resistance: Unknown.

I claim:

1. A new and distinct *Hydrangea macrophylla* plant named 'BCHY-14.003' substantially as herein illustrated and described.

* * * * *